United States Patent [19]

Shah et al.

[11] Patent Number: 4,732,917

[45] Date of Patent: * Mar. 22, 1988

[54] PROCESS FOR PREPARING SUCROSE ENCRUSTED METHYLCELLULOSE PARTICLES FOR USE IN BULK LAXATIVE COMPOSITIONS

[75] Inventors: Dhiren N. Shah, Loveland; Gregory V. Hammer; Jack Domet, both of Cincinnati, all of Ohio

[73] Assignee: Merrell Dow Pharmaceuticals Inc., Cincinnati, Ohio

[ * ] Notice: The portion of the term of this patent subsequent to Dec. 2, 2003 has been disclaimed.

[21] Appl. No.: 900,562

[22] Filed: Aug. 26, 1986

Related U.S. Application Data

[62] Division of Ser. No. 695,984, Jan. 29, 1985, Pat. No. 4,626,287.

[51] Int. Cl.$^4$ ................................................. C08L 1/28
[52] U.S. Cl. ........................... 514/781; 106/197.1; 514/57; 514/777; 514/892
[58] Field of Search .............. 106/197.1; 514/781, 514/892, 57, 777

[56] References Cited

U.S. PATENT DOCUMENTS

| | | | |
|---|---|---|---|
| 2,602,042 | 7/1952 | Abbott | 514/57 |
| 2,701,782 | 2/1955 | Culter | 106/197.1 |
| 2,707,153 | 4/1955 | Bettman | 426/103 |
| 2,824,009 | 2/1958 | Lindow | 426/103 |
| 4,293,570 | 10/1981 | Vadasz | 426/103 |
| 4,444,761 | 4/1984 | Spiller | 517/57 |
| 4,459,280 | 7/1984 | Colliopoulos et al. | 424/35 |
| 4,548,806 | 10/1985 | Colliopoulos et al. | 424/35 |
| 4,626,287 | 12/1986 | Shah et al. | 106/197.1 |

FOREIGN PATENT DOCUMENTS

| | | |
|---|---|---|
| 562196 | 8/1958 | Canada . |
| 189886 | 8/1986 | European Pat. Off. . |
| 8602728 | 5/1986 | Greece . |
| 61-176528 | 8/1986 | Japan . |
| 698661 | 10/1953 | United Kingdom . |
| 1280150 | 7/1982 | United Kingdom . |
| 2097804 | 11/1982 | United Kingdom . |

OTHER PUBLICATIONS

Food Colloids, H. D. Graham, ed., AUl Publishing Co., Inc., Westport, Conn., 1977.

*Primary Examiner*—Ronald W. Griffin
*Attorney, Agent, or Firm*—Stephen L. Nesbitt

[57] ABSTRACT

The present invention relates to an improved process for preparing sucrose encrusted methylcellulose particles which readily disperse in cold aqueous liquids. These encrusted particles are suitable for use in bulk laxative compositions. In the improved process, hot sucrose syrup is mixed with powdered methylcellulose, dried and milled.

16 Claims, No Drawings

PROCESS FOR PREPARING SUCROSE ENCRUSTED METHYLCELLULOSE PARTICLES FOR USE IN BULK LAXATIVE COMPOSITIONS

CROSS REFERENCE TO RELATED APPLICATION

This is a divisional of application Ser. No. 695,984, filed Jan. 29, 1985, now U.S. Pat. No. 4,626,287.

The present invention relates to an improved process for preparing sucrose encrusted methylcellulose particles which readily disperse in cold aqueous liquids.

BACKGROUND OF THE INVENTION

It has been long known that cellulose ethers, such as carboxymethylcellulose and methylcellulose are effective bulk laxatives. The cellulose ethers relieve constipation by increasing the bulk of the stool, increasing the water content of the stool, and it is believed, by a lubricating effect on the stool.

Previously, cellulose ethers have been administered as bulk laxatives in the form of tablets, powders and suspensions in highly concentrated sugar solutions. Each of these methods of administration has significant disadvantages which have limited the acceptance of these products by consumers.

Tableted cellulose ethers, for example, do not readily dissolve in the digestive tract because these cellulose ethers are highly hygroscopic. The outer portion of the tablet quickly forms a gel-like hydrate which prevents break up of the tablet and greatly retards hydration of the interior portions of the tablet. Accordingly, the tablet is often excreted as an intact soft gel mass. Although some laxative effect is produced by such gel masses, the cellulose ether is most effective when dispersed uniformly throughout the stool. Thus, when employed in tablet form, cellulose ethers have reduced efficacy as bulk laxatives.

Cellulose ethers have also been administered orally as powders. Such powders often exhibit the same type of gelation as tablets, i e , the individual particles lump together and remain partially undissolved as they pass through the digestive tract. Moreover, administration of cellulose ethers in powdery form has caused nausea, cramping and vomiting in some patients Accordingly, cellulose ethers are not advantageously administered in powder form.

Cellulose ethers have also been administered as bulk laxatives as suspensions of the cellulose ether in water containing high concentrations of sucrose or other sugars and a flavoring. The sugar competes with the cellulose ether for the available water, thereby preventing the cellulose ether from hydratinq sufficiently to form gels. administration of cellulose ethers in such form has the advantage that the cellulose ether is sufficiently dispersed that it does not form significant amounts of lumps in the digestive tract. Unfortunately, however, such suspensions are very thick and semi-gelatinous. As such, the are visually unappealing. More significantly, due to their slimy mouth feel and extreme sweetness, such suspensions are quite unpalatable. Accordingly, such cellulose ether suspensions have not gained significant consumer acceptance Accordingly, it would be desirable to provide a cellulose ether composition useful as a bulk laxative, which composition is palatable and not visually displeasing and which is administered without the formation of significant amounts of lumps or gels. This can be readily accomplished by adding water or another aqueous liquid to a dry powder mix of a water-soluble cellulose ether and a dispersing/sweetening component, typically sugar. This technology is already known in the prior art, for example, South African Pat. No. 84 1044, published Sept. 26, 1984.

These compositions, however, are not entirely acceptable because a single dose will typically have about 400 calories of nutritive value primarily due to the high sugar content. Such high caloric value is a detracting feature to the average consumer and is unacceptable in users suffering from blood sugar disorders, including diabetics. This is all the more unacceptable because the elderly, who commonly suffer from constipation and are frequent users of laxatives, also commonly exhibit a variety of blood sugar disorders which are aggravated by the consumption of large quantities of sugar.

The caloric content of these compositions can be reduced if, instead of adding granulated sugar to the cellulose ether laxative composition, the sugar is instead used to form a crust around the individual cellulose ether granules. Sugar encrusted cellulose ether particles provide for a product which is readily dispersible in cold aqueous liquids and which result in laxative compositions having substantially less sugar content and less caloric value.

Applicants first prepared the sucrose encrusted cellulose ether particles by dry mixing sugar and cellulose ether, subsequently wet granulating with a small amount of water, and finally drying the wet mixture. Encrusted cellulose ether particles prepared in this way in small laboratory batches are indeed readily dispersible in cold aqueous liquids. However, encrusted particles prepared in this way suffer serious limitations when prepared in large quantities at high speeds using high-tech, production scale equipment. For example, Applicants discovered that the agitation of these particles in a fluid bed dryer apparently destroyed the sugar encrustation and resulted in an end product which would not disperse in cold aqueous liquids. Moreover, when these encrusted particles were milled in a production scale, high-speed mill, the high sugar content "blinded" the milling screen and prevented efficient operation.

Applicants discovered that if, instead of adding water to a dry mixture of sugar and cellulose ether, hot concentrated sugar syrup was added to dry, powdered cellulose ether, a sugar encrusted cellulose ether particle resulted which caused no processing difficulties on production scale equipment and which readily dispersed in cold aqueous fluids.

SUMMARY

This invention is directed to an improved process for preparing sucrose encrusted cellulose ether particles by mixing hot sucrose syrup with powdered methylcellulose.

DETAILED DESCRIPTION OF THE INVENTION

The term "cellulose ether" as used herein means a water-soluble cellulose ether which is effective as an active agent in a bulk laxative. By "effective as an active agent in a bulk laxative" is meant that the cellulose ether measurably increases the bulk, water content or the frequency of the stools of patients to whom it is administered. Such cellulose ethers include, for example, sodium carboxymethylcellulose, methylcellulose, hydroxypropylmethylcellulose, hydroxyethylmethylcellulose, hydroxypropylcellulose and hydroxyethylcellulose. The particular substituent and amount of substitution is not particularly critical as long as the resulting cellulose ether is edible, water-soluble and effective as an active agent in bulk laxative However, this invention is particularly useful when the cellulose ether is one which is soluble but poorly dispersible in water, such as carboxymethylcellulose, or which is soluble, poorly dispersible in cold water but readily dispersible in hot water, such as methylcellulose or hydroxypropylmethylcellulose. The molecular weight of the cellulose ether is not especially critical. The preferred cellulose ether is methylcellulose, preferably methylcellulose of about 4800 cps.

The cellulose ether to be encrusted should be both dry and in powdered form. By dry, Applicants do not mean free of water in the absolute sense but rather substantially free of water so that the individual granules do not adhere to each other and so that the powder flows easily when poured. By powder, Applicants mean very fine, dustlike particles as the term is understood by those skilled in the art. See, for example, *Remington's Pharmaceutical Sciences,* 16th ed , Mack Publishing Company (1980).

The cellulose ether can be used alone or can be dry mixed with other excipients prior to encrusting the granules with a sugar. When the sugar encrusted cellulose ether particles are to be used in a laxative composition suitable excipients include a sugar such as sucrose or glucose, an artificial sweetener such as saccharin or aspartame, flavorings, colorants, and other agents which would assist in dispersing the cellulose ether upon addition of an aqueous fluid. Such dispersing agents are generally known in the prior art, for example, South African Pat. No. 84-1044, published on September 26, 1984.

The sugar used to encrust the cellulose ether can be any natural sugar or combination of sugars such as sucrose, glucose, fructose or corn syrup solids. The preferred sugar is sucrose. When the sugar encrusted cellulose ether particles are to be used in a laxative composition, the sugar to be used in the crust can be mixed with other suitable excipients such as synthetic sweeteners including saccharin, sodium cyclamate and aspartame, flavorings, colorants, and other agents which would assist in dispersing the cellulose ether upon addition of an aqueous fluid. Such dispersing agents are generally known in the prior art, see South African Pat. No. 84-1044, published on September 26, 1984.

While any amount of sugar can be used to encrust the cellulose ether granules, when the encrusted particles are to be used in a laxative composition, the amount of sugar should be sufficient to disperse the cellulose ether particles when added to a cold aqueous solution but should not render the resulting dispersion unpalatably sweet. Preferably, the amount of sugar will comprise from 20% to 90% of the weight of the resulting encrusted particle. More preferably, the sugar will comprise 33% of the weight of the encrusted particle The encrusted particles are prepared by mixing a hot aqueous solution of the sugar containing any desired excipient with dry cellulose ether granules until an evenly moist product is formed This moist product is dried, preferably in a fluid bed dryer, and subsequently passed through a suitable mill, preferably a high-speed mill. The sugar solution or syrup can be of any concentration but will preferably contain at least 50 percent by weight sugar to prevent excessive hydration of the cellulose ether. The amount of syrup used to moisten the cellulose ether particles will, of course, contain the amount of sugar required to form encrusted particles having the desired sugar content.

When preparing the highly concentrated sugar syrups for use in the process of this invention, it is desirable to heat the aqueous media in order to completely dissolve the sugar within a short period of time. Applicants have discovered that if the resulting hot syrup is used to moisten the cellulose ether granules, the resulting encrusted particles are more desirable for use in a bulk laxative composition than are encrusted particles prepared with, for example, room temperature syrup primarily because the resulting encrusted particles prepared by the improved process are more readily dispersible in cold water. Where the syrup is allowed to cool prior to mixing with the cellulose ether, a gelatinous mass results which, after drying and milling, forms a product unsuitable for use in a laxative composition. Although the temperature of the syrup is not especially critical, best results are obtained when the syrup is substantially above ambient temperature. Preferably, the temperature of the syrup will be above 40° C. and more preferably will be about 60° C. Excessive heating of the syrup will cause undesirable carmalization and should be avoided, however, and temperatures below about 75° C. are recommended. In practice, Applicants have prepared suitable hot syrups by adding the sucrose to boiling water. No additional heating is necessary and the temperature of the resulting syrup is suitably hot for use in the improved process. In a preferred embodiment of the invention, a 60 percent by weight sucrose syrup at 60° C. is used to moisten methylcellulose granules

EXAMPLE 1

Preparation of Sucrose Encrusted Methlcellulose Particles

The title particles are prepared in the following manner:

(a) A 60% (w/w) syrup solution is prepared by adding 52.6 Kg of sucrose to 35 Kg of purified boiling water. The temperature of the resulting syrup is approximately 60° C.

(b) The hot syrup is added to 105.3 Kg of methylcellulose, 4800 cps, in a suitable mixer and processed until evenly moist.

(c) The resulting moist product is dried in a fluid bed dryer.

(d) The dried product is then passed through a suitable high speed mill.

What is claimed is:

1. In a process for preparing a sucrose encrusted hydroxypropylmethylcellulose particle suitable for use in a bulk laxative composition wherein sucrose and hydroxypropylmethylcellulose are mixed in the presence of water the improvement which comprises mixing hot sucrose syrup with powdered hydroxypropylmethylcellulose.

2. In the process of claim 1, the improvement wherein the amount of hot sucrose syrup and the concentration of hot sucrose syrup is selected to provide for a sucrose encrusted hydroxypropylmethylcellulose particle consisting of from 20 to 90 percent by weight sucrose.

3. In the process of claim 1, the improvement wherein the amount of hot sucrose syrup and the concentration of the hot sucrose syrup is selected to provide for a sucrose encrusted hydroxypropylmethylcellulose particle consisting of 33 percent by weight sucrose.

4. In the process of claim 1, the improvement wherein the temperature of the hot sucrose syrup is from 40 to 75° C.

5. In the process of claim 1, the improvement wherein the temperature of the hot sucrose syrup is 60° C.

6. In the process of claim 1, the improvement wherein the concentration of hot sucrose syrup is at least 50 percent by weight sucrose.

7. In the process of claim 1, the improvement wherein the concentration of hot sucrose syrup is 60 percent by weight sucrose.

8. In the process of claim 1, the improvement wherein the hot sucrose syrup consists of 60 percent by weight sucrose and wherein the temperature of the hot sucrose syrup is 60° C.

9. A sucrose encrusted hydroxypropylmethylcellulose particle suitable for use in a bulk laxative composition when prepared by the process of claim 1.

10. A sucrose encrusted hydroxypropylmethylcellulose particle suitable for use in a bulk laxative composition when prepared by the process of claim 2.

11. A sucrose encrusted hydroxypropylmethylcellulose particle suitable for use in a bulk laxative composition when prepared by the process of claim 3.

12. A sucrose encrusted hydroxypropylmethylcellulose particle suitable for use in a bulk laxative composition when prepared by the process of claim 4.

13. A sucrose encrusted hydroxypropylmethylcellulose particle suitable for use in a bulk laxative composition when prepared by the process of claim 5.

14. A sucrose encrusted hydroxypropylmethylcellulose particle suitable for use in a bulk laxative composition when prepared by the process of claim 6.

15. A sucrose encrusted hydroxypropylmethylcellulose particle suitable for use in a bulk laxative composition when prepared by the process of claim 7.

16. A sucrose encrusted hydroxypropylmethylcellulose particle suitable for use in a bulk laxative composition when prepared by the process of claim 8.

* * * * *